(12) United States Patent  
Sreeramagiri

(10) Patent No.: US 7,431,708 B2  
(45) Date of Patent: Oct. 7, 2008

(54) KNEE BRACE HAVING LATERAL/MEDIAL WIDTH ADJUSTMENT

(75) Inventor: Murali Krishna Sreeramagiri, Lake Forest, CA (US)

(73) Assignee: Ossur HF, Reykjavik (IS)

( * ) Notice: Subject to any disclaimer, the term of this patent is extended or adjusted under 35 U.S.C. 154(b) by 301 days.

(21) Appl. No.: 11/230,035

(22) Filed: Sep. 19, 2005

(65) Prior Publication Data

US 2007/0066923 A1    Mar. 22, 2007

(51) Int. Cl.
    *A61F 5/00*    (2006.01)
(52) U.S. Cl. .................... 602/26; 602/5; 602/16
(58) Field of Classification Search .......... 602/5, 602/20, 23, 16, 26; 128/882
    See application file for complete search history.

(56) References Cited

U.S. PATENT DOCUMENTS

| 4,599,998 | A | 7/1986 | Castillo |
| 4,856,501 | A | 8/1989 | Castillo |
| 4,940,044 | A | 7/1990 | Castillo |
| D318,736 | S | 7/1991 | Castillo |
| 5,135,469 | A | 8/1992 | Castillo |
| 5,230,697 | A | 7/1993 | Castillo |
| 5,288,287 | A | 2/1994 | Castillo |
| D357,070 | S | 4/1995 | Castillo |
| D433,756 | S | 11/2000 | Castillo |
| 6,875,187 | B2 | 4/2005 | Castillo |
| 2004/0127825 | A1 | 7/2004 | Castillo |
| 2007/0106189 | A1* | 5/2007 | Salmon et al. ............ 602/20 |

* cited by examiner

*Primary Examiner*—Kim M Lewis  
(74) *Attorney, Agent, or Firm*—Bacon & Thomas, PLLC

(57) ABSTRACT

A knee brace having a femur support section pivotally connected to a tibia support section is provided. The femur support section has a medial frame and a lateral frame, sandwiched between width adjustment plates. The width adjustment plates hold the lateral and medial frames, and are held together by retainer bolts and nuts. The retainer bolts and nuts can be loosened to permit the lateral frame and the medial frame to slide against the width adjustment plates. Thus, the space between the lateral frame and the medial frame can be adjusted according to the size of the wearer's leg.

6 Claims, 2 Drawing Sheets

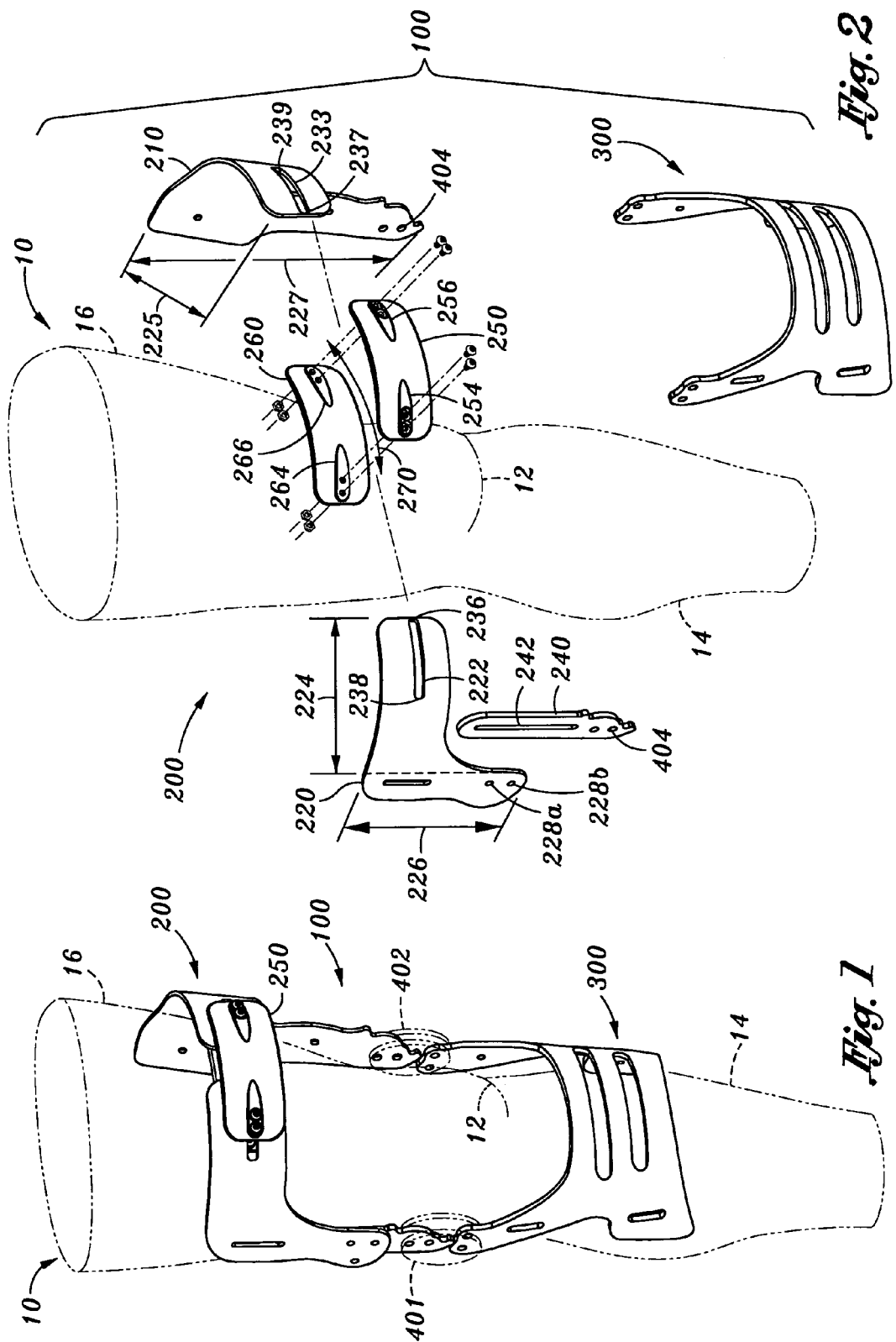

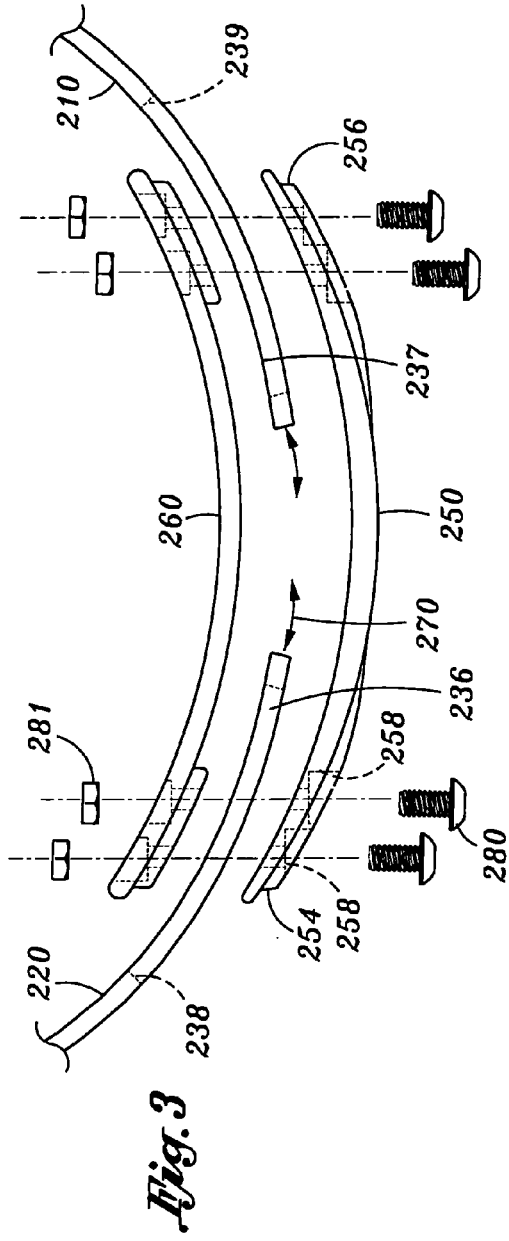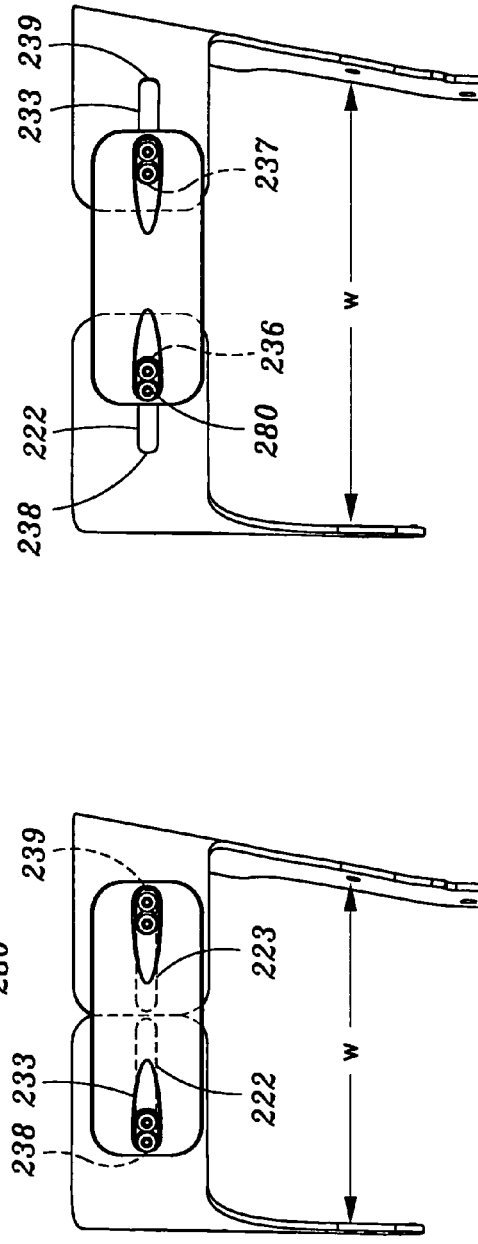

KNEE BRACE HAVING LATERAL/MEDIAL WIDTH ADJUSTMENT

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present invention relates to devices alleviating symptoms of osteoarthritis and other joint dysfunctions. More particularly, the present invention relates to an adjustable knee brace for an osteoarthritic knee joint.

2. Description of the Related Art

Osteoarthritis, also known as degenerative joint disease, is the most common form of arthritis. It is believed that the disease results from a combination of genetic abnormalities and joint injuries. An affected joint progressively loses cartilage, and as a result, the tissue that lines the joint can become inflamed, the ligaments can loosen, and the associated muscles can weaken. Especially vulnerable are knee joints, where sufferers experience pain, stiffness and swelling, and become unable to perform basic life functions such as walking.

Osteoarthritis can be treated with prescription drugs, homeopathic remedies, total joint replacements, and braces. A patient suffering from osteoarthritis in the knee can be fitted with a knee brace whereby support is provided to allow reasonable ambulatory activity without undue risk of injury. Knee bracing does not cure osteoarthritis, but there are indications that the severity of the symptoms may be reduced by bracing because physical forces upon the joint are reduced.

Knee braces are frequently fitted to the exact measurements of the patient, and a properly adjusted brace can accommodate the shape, size, and angle between the femur and the tibia for maximum comfort. However, custom fit knee braces are expensive because each one must be custom manufactured to order.

In order to bring the advantages of the knee brace, namely the non-invasive treatment of osteoarthritis, to a broader spectrum of individuals, knee braces manufactured from common i.e. universal components have been developed. However, these knee braces typically cannot properly accommodate each and every different leg configuration.

Due to this problem in the art, a number of adjustable knee braces have been developed. Among the changes an osteoarthritic knee undergoes is that the body tries to compensate for the degenerative joint and migrate laterally or outwardly, or it may migrate inwardly or medially, with the former condition often referred to as "bowlegged" and the latter referred to as "knock-kneed." When either event occurs, the leg experiences a corresponding curvature, and the wearer continues to suffer pain and discomfort. In order to accommodate such a leg configuration, knee braces angularly adjustable to overcome leg curvature have been developed.

However, other parameters for adjustment have not been possible in such prior knee braces. Accordingly, a primary object of the present invention is to provide a knee brace for the treatment of osteoarthritis that is capable of accommodating a wide variety of leg widths. Another object of the present invention is to provide a knee brace capable of both width adjustment and angular adjustment for maximum comfort of the wearer. Still another object of the present invention is to provide a knee brace that is easily adjustable by the wearer or healthcare professionals. Yet another object of the present invention is to provide an adjustable knee brace that can be constructed of common, universal components so as to simplify the initial fitting as well as subsequent repairs.

BRIEF SUMMARY

An adjustable knee brace for supporting the leg of an osteoarthritic or another individual suffering from a dysfunctional knee joint is disclosed. The brace is comprised of an upper brace supporting the femur, or thigh, portion of the leg, and a lower brace supporting the tibia, or shin, portion of the leg. The upper brace and the lower brace are in a pivoting relationship about a hinge component.

The upper brace includes a lateral frame and a medial frame. The lateral frame connects directly to the hinge component, while the medial frame has an angle adjustment arm which enables the knee brace to be angularly adjusted to accommodate legs where the tibia and femur bend inwardly, or where the tibia and femur bend outwardly. The angle adjustment arm is slidably engaged to the medial frame, and in a pivoting relationship with the lower brace about the hinge component.

The width across the lateral frame and the medial frame is adjustable. A lateral frame adjustment slot and a medial frame adjustment slot is situated on the lateral frame and the medial-frame, respectively, and is in a sliding relationship with an outer width adjustment plate and an inner width adjustment plate. A retaining bolt secures the outer width adjustment plate, the lateral frame and the medial frame, and the inner width adjustment plate, in place, by a retaining nut that is threaded thereon.

By tightening the retaining bolt against the retaining nut, the lateral frame and the medial frame are secured in place, while loosening the same will permit adjustment of the lateral frame and the medial frame. This sliding adjustment enables the knee brace to accommodate a wide range of leg widths.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a front perspective view of a knee brace in place on a leg, the leg and the hinge component shown in phantom;

FIG. 2 is an exploded perspective view of the knee brace shown in FIG. 1, depicted in relation to a leg, the leg shown in phantom;

FIG. 3 is an exploded top elevation view of the knee brace shown in FIG. 1;

FIG. 4a is a front view of an adjustable femoral frame fully contracted; and

FIG. 4b is a front view of an adjustable femoral frame fully extended.

DETAILED DESCRIPTION

The detailed description set forth below in connection with the appended drawings is intended as a description of the presently preferred embodiment of the invention and is not intended to represent the only form in which the present invention may be constructed or utilized. It is to be understood, however, that the same or equivalent functions may be accomplished by different embodiments that are also intended to be encompassed within the spirit and scope of the invention.

With reference to FIGS. 1 and 2, the presently disclosed adjustable knee brace 100 with respect to a wearer's leg 10 is shown. Leg 10 is anatomically comprised of femur (thigh) section 16, knee 12, and tibia (shin) section 14. Femur section 16 is braced by femoral frame 200 and is in a pivoting relationship with tibial frame 300, which braces tibia section 14. Such a pivoting relationship is enabled by hinge components 401 and 402, which preferably are ratio swing hinges constructed according to the disclosure in U.S. Pat. No. 4,940,044, owned by the current Assignee, the disclosure of which is expressly incorporated herein in its entirety by reference. Such hinge components 401 and 402 are designed to closely simulate the rotational movement of the tibia relative the femur, and essentially simulate normal knee movements. All connections herein to hinge components 401 and 402 are as described in the referenced patent. Those skilled in the art will recognize that other conventional hinge constructions are clearly contemplated for use herein.

Referring specifically to FIG. 2, an exploded view of the knee brace 100 is shown. Femoral frame 200 is comprised of medial frame 220, lateral frame 210, inner width adjustment plate 260, and outer width adjustment plate 250.

Medial frame 220 has a horizontally elongate section 224 and vertically elongate section 226. Horizontally elongate section 224 includes a width adjustment slot 222 which extends substantially across horizontally elongate section 224. Furthermore, horizontally elongate section 224 is preferably formed in an arcuate configuration to accommodate the shape of leg 10, specifically the curvature of femur section 16 so as to minimize the profile resulting from and the obstruction caused by the presence of knee brace 100.

Vertically extending section 226 is comprised of upper angular adjustment bolt securing hole 228a, and lower angular adjustment bolt securing hole 228b. Angle adjustment arm 240 has a vertically elongate angle adjustment slot 242, which slidably engages medial frame 220 at angular adjustment bolt securing holes 228a and 228b. Angle adjustment retaining bolts (not shown) are inserted through angle adjustment holes 228a and 228b and angle adjustment slot 240. In its most extended state, the upper end of angle adjustment slot 242 corresponds in position to that of upper angular adjustment bolt securing hole 228a. In its most contracted state, the lower end of angle adjustment slot 242 corresponds in position to that of lower angular adjustment bolt securing hole 228b. Thus, the effective height of the medial side of knee brace 100 can be adjusted, and accordingly, adjustable for bow-legged and knock-kneed legs, a condition characterized by the tibia angling towards the medial side of the leg or the lateral side of the leg. By tightening the angle adjustment retaining bolt, the position of the angle adjustment arm 240 is secured relative to the medial frame 220. An analogous angular adjustment is disclosed in U.S. Pat. No. 6,875,187, the disclosure of which is expressly incorporated by reference in its entirety herein.

Lateral frame 210, similar to its counterpart medial frame 220, has a horizontally elongate section 225 and a vertically elongate section 227. Horizontally elongate section 225 includes a width adjustment slot 233 which extends substantially across horizontally elongate section 225. Like the horizontally elongate section 224 of medial frame 220, the horizontally elongate section 225 of lateral frame 210 is preferably formed having an arcuate configuration to accommodate the shape of leg 10. Unlike medial frame 220, however, lateral frame 210 has an extended vertically elongate section to compensate in height for the lack of an angle adjustment arm. Instead, the lower end of lateral frame 210 has hinge connecting holes 404 to the hinge component 401 shown in FIG. 1, whereas the medial frame 210 has no hinge connecting holes; the hinge connecting holes 404 being on the angle adjustment arm 240.

With reference to FIGS. 2, 3, 4a, and 4b, the details of the width adjustment mechanism will be explained. Specifically referring to FIGS. 2 and 3, width adjustment slot 222 has a distal end 238 and a proximal end 236. Lateral frame 210 also has width adjustment slot 233 configured to mirror width adjustment slot 222 on medial frame 220. Lateral frame adjustment slot 222 has a proximal end 237 and a distal end 239.

Outer width adjustment plate 250 has medial extrusion 254 and lateral extrusion 256, and inner width adjustment plate 260 similarly has medial extrusion 264 and lateral extrusion 266. Medial extrusion 264 and lateral extrusion 266 of inner width adjustment plate 260 is configured to abut slightly into width adjustment slots 222 and 233 so as to facilitate a sliding relationship along semicircular horizontal axis 270 with minimal angular deviation from the same.

As illustrated in FIG. 3, medial frame 220 and lateral frame 210 is sandwiched i.e. disposed between outer width adjustment plate 250 and inner width adjustment plate 260. Outer width adjustment plate 250 and inner width adjustment plate 260 include retaining bolt securing holes 258. The sandwiched relationship is maintained by retaining bolt 280, which is passed through retaining bolt securing holes 258 on outer width adjustment plate 250, then through width adjustment slots 222 and 233 on medial frame 220 and lateral frame 210, respectively, then through retaining bolt securing holes 258 on inner width adjustment plate 260, and finally tightened with retaining nut 281. When the width configuration is determined by the user, retaining bolt 280 and retaining nut 281 is tightened to prevent further movement of medial frame 220 and lateral frame 210 against outer width adjustment plate 250 and inner width adjustment plate 260. When the width configuration is to be modified, retaining bolt 280 and retaining nut 281 is loosened.

Now referring to FIGS. 4a and 4b, the width adjustment functionality of femoral brace 200 is shown. In its most extended position as shown in FIG. 4a, retaining bolt 280 is positioned in the most inward location, proximal ends 236 and 237 of width adjustment slots 222 and 233. In its most contracted position as shown in FIG. 4b, retaining bolt 280 is positioned in the most outward location at distal ends 238 and 239 of width adjustment slots 222 and 233. As can be seen, the width 232 of femoral brace 200 can be increased or decreased depending on the relative position of the lateral frame 220 and medial frame 210 with respect to the outer and inner width adjustment plates 250 and 260 shown in FIG. 2. Thus, legs of a variety of widths can be rapidly and securely accommodated with the present inventive device.

The above description is given by way of example, and not of limitation. Given the above disclosure, one skilled in the art could devise variations that are within the scope and spirit of the invention disclosed herein. Further, the various features of the embodiments disclosed can be used alone, or in varying combinations with each other and are not intended to be limited to the specific combination described herein. Thus, the scope of the claims is not to be limited by the illustrated embodiments.

What is claimed is:

1. An adjustable knee brace for supporting the leg of a wearer about the knee joint, comprising:
   a. a lateral femur frame adapted to be situated above said knee joint and configured to conform to the shape of said leg, said lateral femur frame defining a width adjustment slot;
   b. a medial femur frame adapted to be situated above said knee joint and configured to conform to the shape of the leg, said medial femur frame defining a width adjustment slot;
   c. one or more width adjustment plates each defining one or more retainer securing holes, said width adjustment plates slidably engaging said medial femur frame and said lateral femur frame, wherein said width adjustment plates and said lateral femur frame is secured by a retainer passed through said width adjustment slot and said retainer securing hole; and
   d. a tibial frame pivotally engaged with said medial femur frame and said lateral femur frame.

2. The adjustable knee brace as set forth in claim 1, wherein said width adjustment plates independently slidably engages said medial femur frame and said lateral femur frame.

3. The adjustable knee brace as set forth in claim 1, wherein said retainer is a screw threaded through said retainer securing hole and secured with a nut threaded therein.

4. The adjustable knee brace as set forth in claim 1, wherein said medial femur frame and said lateral femur frame are sandwiched between an outer width adjustment plate and an inner width adjustment plate.

5. The adjustable knee brace as set forth in claim 1, wherein said medial frame is comprised of a laterally extending width adjustment section, and a vertically extending angular adjustment section.

6. The adjustable knee brace as set forth in claim 5, further comprising an angle adjustment arm slidably engaging said vertically extending angular adjustment section, said angle adjustment arm pivotally engaging said tibial frame.

* * * * *